United States Patent [19]

Ciganek et al.

[11] Patent Number: 4,751,306

[45] Date of Patent: Jun. 14, 1988

[54] IMIDE INTERMEDIATES FOR THE PREPARATION OF ANALGESIC AND/OR ANTAGONIST OCTAHYDROBENZOFUROISOQUINO-LINES

[75] Inventors: Engelbert Ciganek, Kennett Square, Pa.; Bet-key Wong, Wilmington, Del.

[73] Assignee: E. I. Du Pont de Nemours and Company, Wilmington, Del.

[21] Appl. No.: 774,025

[22] Filed: Sep. 9, 1985

[51] Int. Cl.⁴ .................. C07D 491/06; C07D 491/08; C07D 407/12; C07D 407/14
[52] U.S. Cl. .......................... 546/44; 546/66; 549/291; 549/60; 549/467
[58] Field of Search .................... 546/44, 66

[56] References Cited

U.S. PATENT DOCUMENTS

| | | | |
|---|---|---|---|
| 3,546,227 | 12/1970 | Ginünder et al. | 546/98 X |
| 4,229,467 | 10/1980 | Parker | 549/468 X |
| 4,243,668 | 1/1981 | Ciganek | 546/66 X |
| 4,477,456 | 10/1984 | Ciganek | 546/44 X |

OTHER PUBLICATIONS

Fatome et al., Chem. Abstracts, vol. 87 (1977).

*Primary Examiner*—Mark L. Berch
*Assistant Examiner*—William A. Teoli, Jr.

[57] ABSTRACT

Imide intermediates for the preparation of analgesic and/or antagonist octahydrobenzofuro[3,2-e]-isoquinolines and octahydro-4a,7-ethano- and ethenobenzofuro[3,2-e]isoquinolines and processes for their preparation are provided. These imides have a formula selected from the group consisting of:

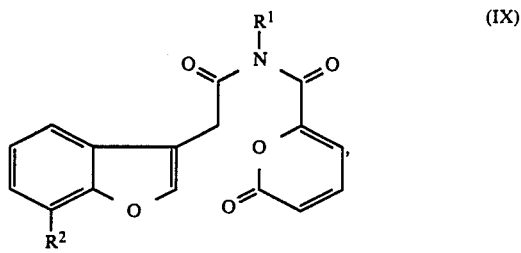

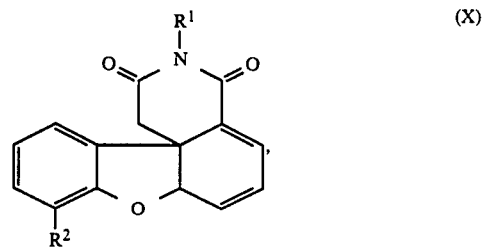

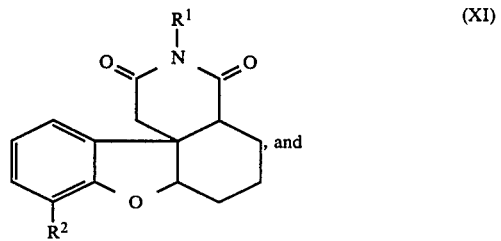

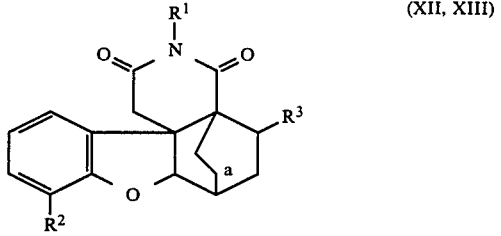

13 Claims, No Drawings

IMIDE INTERMEDIATES FOR THE PREPARATION OF ANALGESIC AND/OR ANTAGONIST OCTAHYDROBENZOFUROISOQUINOLINES

BACKGROUND OF THE INVENTION

1. Field of Invention:

This invention relates to imides and processes for their preparation and more particularly to imide intermediates for the preparation of analgesic and/or antagonist octahydrobenzofuroisoquinolines, processes for preparing the imide intermediates, and processes for preparing the octahydrobenzofuroisoquinolines from the imide intermediates.

2. Prior Art:

Octahydro-1H-benzofuro[3,2-e]isoquinoline analgesic and narcotic antagonistic compounds are disclosed in U.S. Pat. No. 4,243,688 (to Ciganek). These compounds have Formula (Ia):

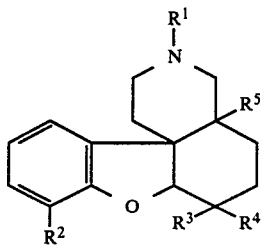

wherein:
$R^1$ is H, $C_1$-$C_{10}$ alkyl, $CH_2$—$R^6$, $C_2H_4(C_6H_4)R^7$, or $(CH_2)_n CN$ where n=1-3;
$R^2$ is H, OH, $C_1$-$C_2$ alkoxy, or $C_2$-$C_{12}$ acyloxy of an alkanoic acid;
$R^3$ is separately H, OH, $CH_3$, $C_1$-$C_2$ alkoxy, $C_2$-$C_{12}$ acyloxy of an alkanoic acid, F, or $N_3$;
$R^4$ is separately H or F;
$R^3$ and $R^4$ in combination are methylene or keto;
$R^5$ is H, OH,

or $OCH_3$;

$R_6$ is $CH{=}C(R^8)(R^9)$, $C{\equiv}CH$, $C_3$-$C_6$ cycloalkyl, 2-thienyl, 2-furyl, 2-tetrahydrofuryl, methyl substituted 2-furyl, or methyl-substituted 2-tetrahydrofuryl;
$R^7$ is $C_1$-$C_3$ alkyl, $OCH_3$, Cl, Br, or F; and
$R^8$ and $R^9$ are independently H, $CH_3$, or Cl.

Utility, dosage formulations, and preferred compounds are disclosed in this patent, as is a process for preparing the compounds. In particular, lactams of Formula (III) are disclosed as intermediates for the preparation of compounds of Formula (Ia) wherein $R^3$, $R^4$, and $R^5$ are all H. In addition, compounds of Formulas (IV) and (V) are disclosed, along with processes for converting (V) to (IV) and for converting (IV) to (III).

Octahydro-4a,7-ethano- and ethenobenzofuro[3,2-e]isoquinoline analgesic and narcotic antagonistic compounds are disclosed in U.S. Pat. No. 4,477,456 (to Ciganek). These compounds have Formula (IIa):

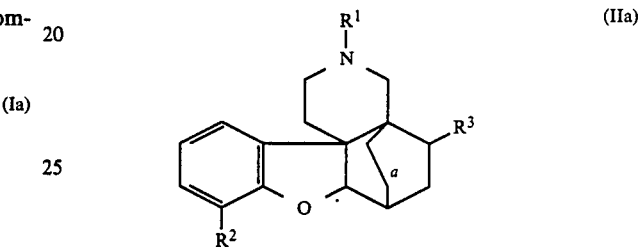

wherein:
$R^1$ is H, $C_1$-$C_{10}$ alkyl, $CH_2$—$R^6$, $C_2H_4(C_6H_4)R^7$, or $(CH_2)_n CN$, in which n=1-3;
$R^2$ is H, OH, $C_1$-$C_2$ alkoxy, or $C_2$-$C_{12}$ acyloxy of an alkanoic acid;
$R^3$ is H, $C_1$-$C_8$ alkyl, or $C(OH)(R^4)(R^5)$;
a is a single bond or a double bond;
$R^4$ is H or $C_1$-$C_8$ alkyl;
$R^5$ is H, $C_1$-$C_8$ alkyl, $C_2$-$C_8$ alkenyl, $C_3$-$C_8$ cycloalkyl, or $(CH_2)_m$—$C_6H_5$ in which m=0-4;
$R^6$ is $CH{=}C(R^8)(R^9)$, $C{\equiv}CH$, $C_3$-$C_6$ cycloalkyl, phenyl, 2-thienyl, 2-furyl, 2-tetrahydrofuryl, methyl substituted 2-furyl, or methyl substituted 2-tetrahydrofuryl;
$R^7$ is H, $C_1$-$C_3$ alkyl, $OCH_3$, Cl, Br, or F; and
$R^8$ and $R^9$ are independently H, $CH_3$, or Cl.

Utility, dosage formulations, and preferred compounds are disclosed in this patent, as is a process for preparing the compounds. In particular, lactams of Formula (VI) below are disclosed as intermediates for the preparation of compounds of Formula (IIa). Compounds of Formula (VI) are prepared from compounds of Formula (IV), disclosed in U.S. Pat. No. 4,243,668.

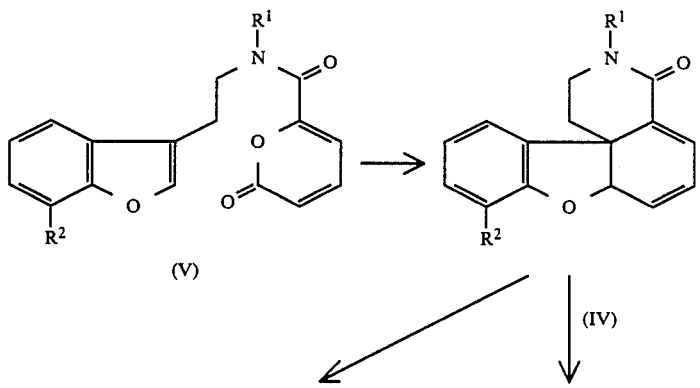

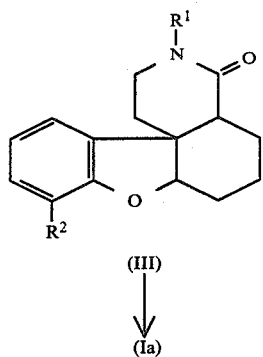

(III)

↓

(Ia)

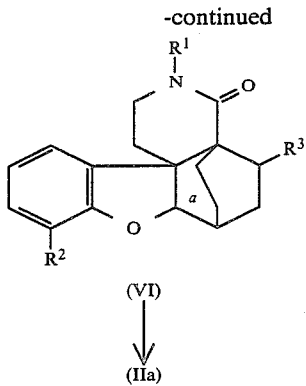

-continued (VI)

↓

(IIa)

SUMMARY OF THE INVENTION

According to the present invention there is provided a compound selected from the group consisting of

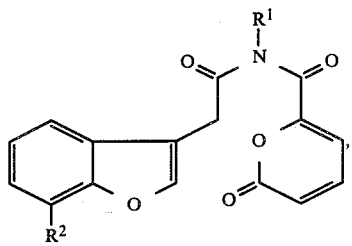

(IX)

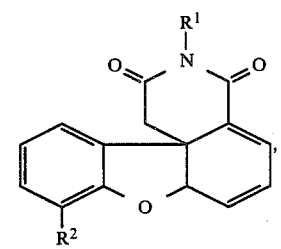

(X)

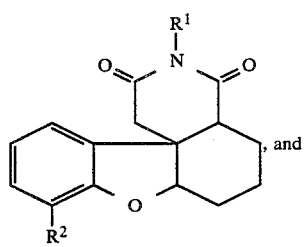

(XI)

, and

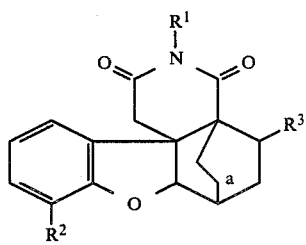

(XII, XIII)

wherein
a is a single bond or double bond;
$R^1$ is $C_1-C_{10}$ alkyl, $CH_2R^6$, $C_2H_4(C_6H_4)R^7$, or $(CH_2)_nCN$ in which n=1-3;
$R^2$ is H, OH, or $C_1-C_2$ alkoxy;
$R^3$ is H, $C_1-C_8$ alkyl, or $COR^4$;
$R^4$ is H, $C_1-C_8$ alkoxy, or $C_1-C_8$ alkyl;
$R^6$ is $CH=C(R^8)(R^9)$, $C\equiv CH$, $C_3-C_6$ cycloalkyl, phenyl, 2-thienyl, 2-furyl, 2-tetrahydrofuryl, methyl substituted 2-furyl, or methyl substituted 2-tetrahydrofuryl;
$R^7$ is H, $C_1-C_3$ alkyl, $OCH_3$, Cl, Br, or F; and
$R^8$ and $R^9$ are independently H, $CH_3$, or Cl.

Also provided are processes for preparing the above compounds and using the above compounds to prepare an analgesic and/or antagonist compound of the formula:

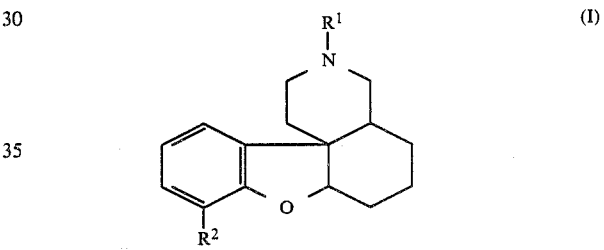

(I)

or

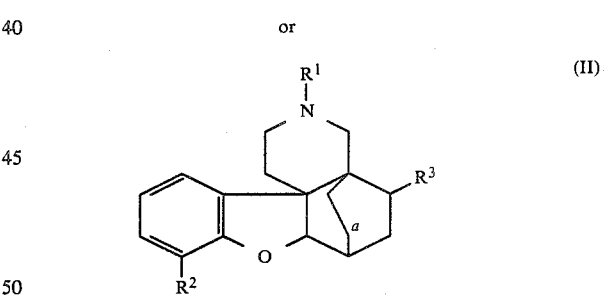

(II)

wherein
a is a single bond or a double bond;
$R^1$ is $C_1-C_{10}$ alkyl, $CH_2R^6$, $C_2H_4(C_6H_4)R^7$ or $(CH_2)_nCN$ in which n=1-3;
$R^2$ is H, OH, or $C_1-C_2$ alkoxy;
$R^3$ is H, $C_1-C_8$ alkyl, or $C(OH)(R^4)(R^5)$;
$R^4$ is H, or $C_1-C_8$ alkyl;
$R^5$ is H, $C_1-C_8$ alkyl, $C_2-C_8$ alkenyl, $C_3-C_8$ cycloalkyl, or $(CH_2)_m-C_6H_5$ in which m=0-4;
$R^6$ is $CH=C(R^8)(R^9)$, $C\equiv CH$, $C_3-C_6$ cycloalkyl, phenyl, 2-thienyl, 2-furyl, 2-tetrahydrofuryl, methyl substituted 2-furyl, or methyl substituted 2-tetrahydrofuryl;
$R^7$ is H, $C_1-C_3$ alkyl, $OCH_3$, Cl, Br, or F; and
$R^8$ and $R^9$ are independently H, $CH_3$, or Cl; comprising
(a) heating a compound of Formula (IX) at a temperature in the range of about 50°–300° C. for a time sufficient to obtain substantial Diels-Alder reaction;

(b) contacting and reacting the product of step (a) according to one of the following two steps:
  (i) with catalytic hydrogenation in the liquid phase at a temperature in the range of about 20°–100° C.
  (ii) with an olefin capable of introducing $R^3 = C_1 – C_8$ alkyl or $COR^4$;

(c) optionally contacting and reacting the product of step (b)(ii) with catalytic hydrogenation in the liquid phase at a temperature in the range of about 20°–100° C.; and (d) contacting and reacting the product of step (b) or step (c) with a complex metal hydride in the liquid phase at a temperature in the range of about 25°–150° C.

DETAILED DESCRIPTION OF THE INVENTION

The imides of the invention, their preparation and conversion to the analgesic and/or antagonist compounds of Formula (I) and Formula (II) are shown in Reaction Scheme (1).

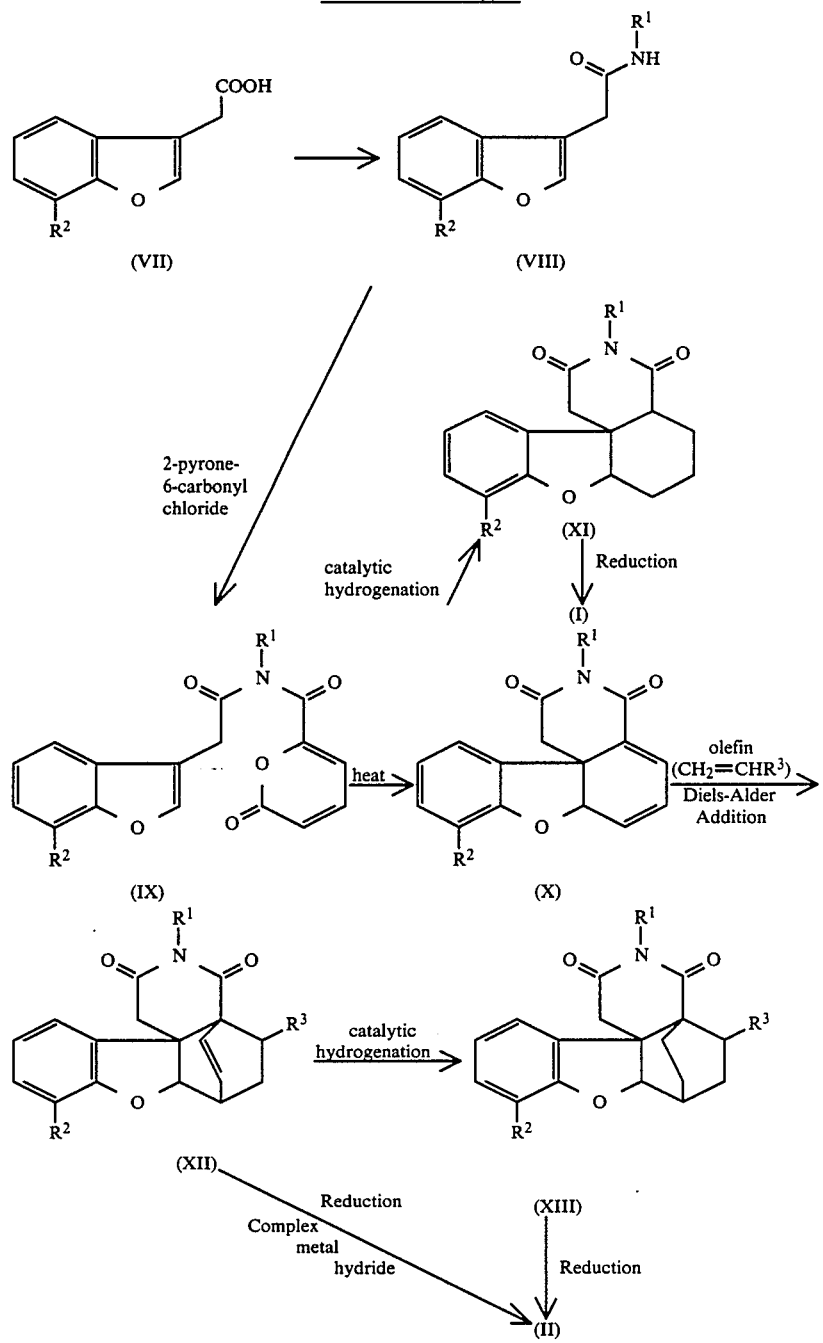

Compounds of Formula (IX) can be prepared by a three-step process from benzofuranacetic acids of Formula (VII), which are disclosed in Ciganek, U.S. Pat. No. 4,243,668. Acids of Formula (VII) are converted to mixed anhydrides or acid chlorides by treatment with an acid chloride such as methyl chloroformate or oxalyl chloride. These acylating agents are then converted to the amides of Formula (VIII) by treatment with an appropriate amine. Such transformations of acids to amides are well known in the chemical literature. Amides of Formula (VIII) can alternatively be prepared by treatment of compounds of Formula (VII) directly with an appropriate amine, with azeotropic removal of water. The amides of Formula (VIII) are then converted to imides of Formula (IX) by treatment with 2-pyrone-6-carbonyl chloride in an appropriate inert solvent such as carbon tetrachloride. Preparation of imides of Formula (IX) are illustrated by Examples 1, 7, and 16.

The cyclic imides of Formula (X) are prepared by the intramolecular Diels-Alder reaction of the corresponding compounds of Formula (IX). This reaction is carried out by heating a compound of Formula (IX) at a temperature in the range of about 50°–300° C. (preferably 50° to 150° C.) for a time sufficient to obtain substantial Diels-Alder reaction. This time can range from several minutes to several hours depending upon the temperature used. The reaction can be carried out in the absence of a solvent or preferably using an inert solvent such as aromatic hydrocarbons, chlorinated aromatic hydrocarbons, and aliphatic or aromatic ethers. The reaction is conveniently carried out at the boiling point of the solvent used.

The conversion of the imides of Formula (IX) to the imides of Formula (X) in this reaction constitutes a significant improvement over the conversion of amides (V) to lactams (IV) as disclosed in U.S. Pat. No. 4,243,668. In the latter reaction, a higher reaction temperature is required to obtain substantial amounts of the product (IV). The higher temperature required in that case can cause appreciable polymerization of the starting amide. Also, the preferred manner of converting the amide to the lactam requires the use of a very dilute solution (0.5–1.0% by weight) of the starting material to avoid dimerization of the product and decreased yields of the desired lactam product. Thus, scale-up may be more difficult. The process disclosed herein, using an imide (IX) in place of an amide, can be carried out at lower reaction temperature, and in more concentrated solution, than that disclosed by the process of U.S. Pat. No. 4,243,668.

The process of this invention, and the intermediate cyclic imides of Formula (X), are illustrated by Examples 2, 8, and 17.

The cyclic imides of Formula (XII) are prepared by the intermolecular Diels-Alder reaction of the corresponding compounds of Formula (X) with an appropriate olefin ($CH_2=CHR^3$) such as acrolein, methyl acrylate, ethylene, or propylene. This reaction can be carried out in the absence of a solvent or using inert solvents such as aromatic hydrocarbons, chlorinated aromatic hydrocarbons, and aliphatic or aromatic ethers. The reaction is carried out at a temperature in the range of about 50° to 250° C. for several minutes to several weeks. To avoid yield loss due to any polymerization of (X), the reaction is preferably carried out in an evacuated steel or glass vessel after the reactants and/or reactant solution has been thoroughly degassed. Undesirable polymerization of the dienophile can also be minimized by the presence of a free radical polymerization inhibitor, such as phenothiazine. This step has the advantages of giving a higher yield of the adduct with the desired stereochemistry of $R^3$ and a lower proportion of undesirable by-products, as compared to the reaction of the corresponding lactam (IV) to give (VI, a=double bond).

The process of this conversion, and the intermediate cyclic imides of Formula (XII), are illustrated by Examples 3, 9, 13, and 18.

The etheno bridge of compounds of Formula (XII) is reduced to an ethano bridge by conventional catalytic hydrogenation in the liquid phase at a temperature of about 20° to 100° C., preferably in the range of about 20° to 50° C. Conventional hydrogenation catalysts such as Raney nickel, platinum and palladium, any of which can be supported on suitable carriers such as carbon or alumina, can be used. The reaction is preferably carried out with an excess of hydrogen and under comparatively mild conditions of temperature, e.g., 25° C., and atmospheric pressure, in order to reduce the double bond but not the benzene ring.

The process of this conversion, and the resulting cyclic imides of Formula (XII), are illustrated by Examples 4, 10, and 14.

The compounds of Formula (X) are converted to the compounds of Formula (XI) by conventional catalytic hydrogenation in the liquid phase at temperatures of about 20° to 100°, preferably in the range of about 20° to 50°. Conventional hydrogenation catalysts such as Raney Nickel, platinum and palladium, any of which can be supported on suitable carriers such as carbon or alumina, can be used. The reaction is preferably carried out with an excess of hydrogen and under comparatively mild conditions of temperature, e.g., 25° C., and at atmospheric pressure, in order to reduce the double bonds but not the benzene ring.

The process of this conversion, and the resulting cyclic imides of Formula (XI), are illustrated by Example 19.

The cyclic imides of Formula (XII) are converted to octahydro-4a,7-ethenobenzofuro[3,2-e]isoquinolines of Formula (II), wherein a is a double bond, by reduction with a complex metal hydride such as lithium aluminum hydride. Likewise, cyclic imides of Formula (XIII) are converted to octahydro-4a,7-ethanobenzofuro[3,2-e]isoquinolines of Formula (II), wherein a is a single bond, by the same procedure. Also, cyclic imides of Formula (XI) are converted to octahydrobenzofuro[3,2-e]isoquinolines of Formula (I) by the same procedure. To obtain a satisfactorily rapid reaction rate, the reaction with a complex metal hydride should be carried out in the liquid phase at a temperature in the range of about 25° to 150° C., preferably in the range of about 50° to 100° C. A preferred method of carrying out the reaction is solvent reflux, whereby the reaction is effected at essentially the boiling point of the solvent used, such as tetrahydrofuran.

If $R^3$ of (XII) or (XIII) is an aldehyde or ester group, then $R^3$ of the product (II) will be $CH_2OH$. If $R^3$ of (XII) or (XIII) is a ketone, then $R^3$ of the product (I) will be the corresponding secondary alcohol. The process of this conversion is illustrated by Examples 5, 6, 11, 12, 15, and 20.

The compounds and processes of the invention are illustrated by the following examples, in which all percentages are by weight unless otherwise indicated, and all temperatures are in degrees Celsius.

In these molecules (except for VII, VIII, and IX), d and l optical isomers occur as racemic mixtures which can be resolved by known methods (e.g., Eliel, *Stereo-*

*chemistry of Carbon Compounds*, McGraw-Hill, 1962, page 21).

The preferred absolute and relative stereochemistry of compounds of Formulas (X) through (XIII) is that leading to compounds of Formulas (I) and (II) with the absolute and relative stereochemistry shown below.

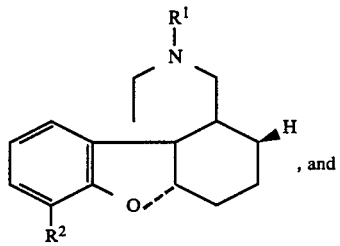

(I)

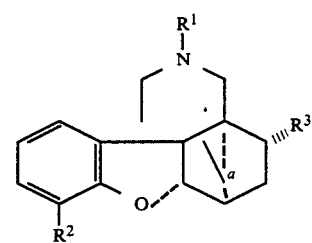

(II)

EXAMPLE 1

N-Cyclopropylmethyl-N-(2-pyrone-6-carbonyl)-7-methoxy-3-benzofuranacetamide [(IX), $R^1$=Cyclopropylmethyl, $R^2$=OCH$_3$]

Part A

A solution of 0.505 g of methyl chloroformate in 3 ml of methylene chloride was added slowly at $-5°$ to a mixture of 1.00 g of 7-methoxy-3-benzofuranacetic acid, 0.815 g of N,N-diisopropylethylamine and 10 ml of methylene chloride. After the addition was complete, the mixture was stirred at $-5°$ for 0.5 hour and then at 10° for 1.5 hours. The solvents were removed and the residue was partitioned between methylene chloride and dilute hydrochloric acid. The organic layer was washed with concentrated ammonium chloride solution, dilute sodium hydroxide solution, and brine. Removal of the solvent from the dried solution gave 1.19 g (93%) of the mixed anhydride of 7-methoxy-3-benzofuranacetic acid and methylcarbonic acid. NMR spectrum (200 mHz in CDCl$_3$): δ3.67 (s, 2H), 3.70 (s, 3H), 3.97 (s, 3H), 6.78 (d/d, J=7.0/6.5 Hz, 1H), 7.15 (m, 2H) and 7.62 (s, 1H). IR spectrum: 1750 cm$^{-1}$, 1740 cm$^{-1}$, among others.

Part B

A mixture of 1.29 g of the mixed anhydride prepared according to Part A, 1.0 g of N-cyclopropylmethylamine and 3 ml of N,N-diisopropylethylamine, contained in an evacuated, sealed Carius tube, was heated to 160° for 24 hours. The solvents were removed and the residue was partitioned between methylene chloride and concentrated hydrochloric acid solution. The organic phase was washed with concentrated ammonium chloride solution, dilute sodium hydroxide solution and brine. Removal of the solvent from the dried solution gave 1.14 g (88%) of N-cyclopropylmethyl-7-methoxy-3-benzofuranacetamide as a solid. NMR spectrum (200 mHz in CDCl$_3$): δ0.15 (m, 2H), 0.44 (m, 2H), 0.85 (m, 1H), 3.10 (t, J=3.5 Hz, 2H), 3.67 (s, 2H), 4.05 (s, 3H), 5.70 (broad s, 1H), 6.88 (d/d, J=7.0/6.5 Hz, 1H), 7.2 (m, 2H) and 7.65 (s, 1H). IR spectrum (Nujol): 1645 cm$^{-1}$, among others.

Alternatively, this product can be prepared by following the procedure of Example 7 Parts A and B, but using cyclopropylmethyl amine in place of benzylamine.

Part C

A mixture of 3.0 g of the product prepared according to Part B, 2.39 g of 2-pyrone-6-carbonyl chloride, and 23 ml of carbon tetrachloride was heated under reflux for 18 hours. The mixture was then cooled to 25° and partitioned between methylene chloride and water. The water layer was extracted with methylene chloride and the combined organic layers were washed with concentrated sodium bicarbonate solution and brine. Removal of the solvent from the dried solution gave 4.6 g of the crude title compound as an oil. NMR spectrum (200 mHz in CDCl$_3$): δ0.35 (m, 2H), 0.55 (m, 2H), 1.15 (m, 1H), 3.74 (d, J=7 Hz, 2H), 4.00 (s, 3H), 4.05 (s, 2H), 6.46 (d, J=7 Hz, 1H), 6.78 (d, J=7 Hz, 1H), 6.83 (d/d, J=7.0/6.5 Hz, 1H), 7.1-7.3 (m, 2H), 7.41 (d/d, J=8.0/6.5, 1H) and 7.70 (s, 1H). IR spectrum (neat): 1750 cm$^{-1}$, 1730 cm$^{-1}$, 1685 cm$^{-1}$, among others.

EXAMPLE 2

3-Cyclopropylmethyl-1,7a-dihydro-9-methoxybenzofuro[3,2-e]isoquinoline-2,4-dione [(X), $R^1$=Cyclopropylmethyl, $R^2$=OCH$_3$]

A solution of 3.04 g of the product of Example 1 in 25 ml of toluene was heated under reflux for 24 hours. Removal of the solvents from the filtered solution and crystallization of the residue (2.29 g) from acetonitrile gave 1.3 g (48%) of the title compound, mp 166°-167°. NMR spectrum (360 mHz in CDCl$_3$): δ0.40-1.30 (m, 5H), 2.95, 2.85 (ABq, J=15.64 Hz, 2H), 3.82 (d/d, J=13/7 Hz, 1H), 3.89 (s, 3H), 3.90 (d/d, J=13/7 Hz, 1H), 5.50 (d/d, J=4.3/0.2 Hz, 1H), 6.15 (d/d/d, J=10.0/2.0/0.2 Hz, 1H), 6.22 (d/d, J=10.0/4.3/0.2 Hz, 1H), 6.70-6.80 (m, 3H) and 7.25 (d, J=6 Hz, 1H). IR Spectrum (neat): 1720 cm$^{-1}$, 1665 cm$^{-1}$, among others. Mass spectrum: m/z calcd for C$_{20}$H$_{19}$NO$_4$: 337.1314; found, 337.1316. Anal. calcd for C$_{20}$H$_{19}$NO$_4$: C, 71.23; H, 5.64; N, 4.15; O, 18.99. Found: C, 71.16; H, 5.84; N, 4.03; O, 18.79.

In another experiment, the half-life for the intramolecular Diels-Alder reaction was found to be approximately 2 hours at 111°. By comparison, cyclization of N-cyclopropylmethyl-N-(7-methoxy-3-benzofuraneethyl)-2-pyrone-6-carboxamide (U.S. Pat. No. 4,243,668) requires heating to 215° (half-life ca. 1 hour).

EXAMPLE 3

3-cyclopropylmethyl-1,3,5,6,7,7a-hexahydro-9-methoxy-5-methoxycarbonyl-4,7a-ethenobenzofuro[3,2-e]isoquinoline-2,4-dione [(XII), $R^1$=Cyclopropylmethyl, $R^2$=OCH$_3$, $R^3$=COOCH$_3$, a=double bond]

A mixture of 1.5 g of the product prepared according to Example 2, 0.01 g of phenothiazine, and 6 ml of methyl acrylate was heated under reflux for 36 hours. Removal of the solvent followed by chromatography on silica gel with 3:1 ethyl acetate/hexane gave 1.6 g of a 13:1 mixture of two isomeric adducts. Crystallization from acetonitrile gave 0.85 g (45%) of the title compound, mp 160°–161°, as a single isomer. NMR spectrum (360 mHZ in CDCl$_3$): δ0.45–0.6 (m, 4H), 1.3–1.4 (m, 1H), 1.80 (m, 1H), 2.03 (t/d, 1H), 3.14 (d/d, J=9/4 Hz, 1H), 3.23, 2.95 (ABq, J=18.5 Hz, 2H), 3.3–3.4 (m, 1H), 3.58 (s, 3H), 3.75 (d/d, J=13/7 Hz, 1H), 3.83 (s, 3H), 3.98 (d/d, J=13/7 Hz, 1H), 4.55 (d, J=3.23 Hz, 1H), 6.33 (s, 1H), 6.34 (d, J=2 Hz, 1H) and 6.6–6.8 (m, 3H). IR spectrum (Nujol): 1760 cm$^{-1}$, 1735 cm$^{-1}$, 1690 cm$^{-1}$, among others. Mass Spectrum: m/z calcd for C$_{24}$H$_{25}$NO$_6$, 423.1682; found, 423.1654.

In a separate experiment, the pseudo half-life of the Diels-Alder addition at 100° was found to be 1.8 hours. By comparison, the pseudo half-life for the corresponding Diels-Alder addition to 3-cyclopropylmethyl-2,3-dihydro-9-methoxybenzofuro[3,2-e]isoquinolin-4(7aH)-one, as described in U.S. Pat. No. 4,477,456, was 4.4 hours, and the ratio of desired to undesired cycloadduct was about 3:1.

EXAMPLE 4

3-Cyclopropylmethyl-1,3,5,6,7,7a-hexahydro-9-methoxy-5-methoxycarbonyl-4a,7-ethanobenzofuro[3,2-e]isoquinoline-2,4-dione [(XIII), R$^1$=Cyclopropylmethyl, R$^2$=OCH$_3$, R$^3$=COOCH$_3$, a=single bond].

A solution of 0.50 g of the product of Example 3 in 20 ml of tetrahydrofuran was stirred with 0.5 g of 10% palladium on charcoal under hydrogen for 25 hours. Removal of the solvent from the filtered solution gave 0.5 g (99%) of the title compound. NMR spectrum (200 mHz in CDCl$_3$): δ0.35–0.6 (m, 3H), 1.1–1.4 (m, 3H), 1.5–1.85 (m, 3H), 1.9–2.1(m, 1H), 2.2–2.45 (m, 2H), 3.0 (m, 1H), 2.97, 3.07 (ABq, J=14 Hz, 2H), 3.63 (s, 3H), 3.65 (d/d, J=13/7 Hz, 1H), 3.89 (s, 3H), 3.90 (d/d, J=13/7 Hz, 1H), 4.48 (d, J=2 Hz, 1H), 6.6 (d/d, J=6.6/2.0 Hz, 1H) and 6.75 (m, 2H). IR spectrum: 1745 cm$^{-1}$, 1730 cm$^{-1}$, 1685 cm$^{-1}$, among others.

EXAMPLE 5

3-Cyclopropylmethyl-5-hydroxymethyl-9-methoxy-1,2,3,4,5,6,7,7a-octahydro-4a,7-ethanobenzofuro[3,2-e]isoquinoline [(II), R$^1$=Cyclopropylmethyl, R$^2$=OCH$_3$, R$^3$=CH$_2$OH, a=single bond]

A mixture of 0.50 g of the product of Example 4, 0.67 g of lithium aluminum hydride, and tetrahydrofuran was heated under reflux for 48 hours. Conventional workup gave 0.29 g (67%) of an oil, the NMR and IR spectra of which were identical to those of the title compound (U.S. Pat. No. 4,477,456, intermediate in Example No. 9).

EXAMPLE 6

3-Cyclopropylmethyl-5-hydroxymethyl-9-methoxy-1,2,3,4,5,6,7,7a-octahydro-4a,7-ethenobenzofuro[3,2-e]isoquinoline [(II), R$^1$=Cyclopropylmethyl, R$^2$=OCH$_3$, R$^3$=CH$_2$OH, a=double bond]

Following the procedure of Example 5 but using 0.264 g of 3-cyclopropylmethyl-1,3,5,6,7,7a-hexahydro-9-methoxy-5-methoxycarbonyl-4a,7-ethenobenzofuro[3,2-e]isoquinolin-2,4-dione (from Example 3), there was obtained 0.09 g (39%) of a crude product mixture, the NMR spectrum of which showed the major product to be identical with the title compound.

EXAMPLE 7

N-Benzyl-N-(2-pyrone-6-carbonyl)-7-methoxy-3-benzofuranacetamide [(IX), R$^1$=Benzyl, R$^2$=OCH$_3$]

Part A

A solution of 15.0 g of 7-methoxy-3-benzofuranacetic acid in 86 ml of oxalyl chloride was stirred at 25° for 1 hour. Removal of the solvent gave 16.35 g (100%) of crude 7-methoxy-3-benzofuranacetic acid chloride. NMR spectrum (200 mHz in CDCl$_3$): δ4.0 (s, 3H), 4.23 (s, 2H), 6.83 (d, J=7 Hz, 1H), 7.07 (d, J=7 Hz, 1H), 7.18 (d, J=8 Hz, 1H) and 7.68 (s, 1H).

Part B

A solution of 16.35 g of the product from Part A was added to a mixture of benzylamine, 15% aqueous sodium hydroxide solution and methylene chloride at −5° to 0°. The reaction mixture was stirred at 0° for 1 hour and then at 25° for 2 hours, and was worked up by washing with dilute hydrochloric acid solution, 15% aqueous sodium hydroxide solution, and brine. Removal of the solvent from the dried solution gave 21.5 g (100%) of pure N-benzyl-7-methoxy-3-benzofuranacetamide. NMR spectrum (200 mHz in CDCl$_3$): δ3.7 (s, 2H), 4.0 (s, 3H), 4.38 (d, J=7 Hz, 2H), 5.9 (broad s, 1H), 6.83 (d/d, J=7/2 Hz, 1H), 7.1–7.4 (m, 7H) and 7.6 (s, 1H).

Alternatively, this product can be prepared by following the procedure of Example 1 Parts A and B, but using benzylamine in place of cyclopropylmethylamine.

Part C

Following the procedure of Example 1 Part C, but using 3.77 g of N-benzyl-7-methoxy-3-benzofuranacetamide from Part B and 2.23 g of 2-pyrone-6-carbonyl chloride as starting materials, there was obtained 5.04 g (95%) of the title compound. NMR spectrum (200 mHz in CDCl$_3$): δ3.95 (s, 2H), 4.00 (s, 3H), 5.04 (s, 2H), 6.45 (d, J=9 Hz, 1H), 6.70 (d, J=6.5 Hz, 1H), 6.78 (d, J=7 Hz, 1H), 7.00 (d/d, J=8.0/0.5 Hz, 1H), 7.2–7.5 (m, 6H) and 7.6 (s, 1H). IR spectrum (neat): 1750 cm$^{-1}$, 1730 cm$^{-1}$, 1695 cm$^{-1}$, among others.

EXAMPLE 8

3-Benzyl-1,7a-dihydro-9-methoxybenzofuro-[3,2-e]isoquinoline-2,4-dione [(X), R$^1$=Benzyl, R$^2$=OCH$_3$]

Following the procedure of Example 2, but using 5.04 g of N-benzyl-N-(2-pyrone-6-carbonyl)-7-methoxy-3-benzofuranacetamide (from Example 7), there was obtained 3.70 g (82%) of the title compound as an oil. NMR spectrum (200 mHz in CDCl$_3$): δ2.85, 2.95 (ABq, J=15 Hz, 2H), 3.85 (s, 3H), 5.1 (s, 2H), 5.44 (s, 1H), 5.95 (d, J=7 Hz, 1H), 6–6.2 (m, 2H), 6.5 (t, J=7 Hz, 1H), 6.7 (d, J=7 Hz, 1H), 7.2 (d, J=6 Hz, 1H) and 7.3–7.6 (m, 5H). IR spectrum: 1730 cm$^{-1}$, 1680 cm$^{-1}$, among others.

EXAMPLE 9

3-Benzyl-1,3,5,6,7,7a-hexahydro-9-methoxy-5-methoxycarbonyl-4a,7-ethenobenzofuro[3,2-e]-isoquinoline-2,4-dione [(XII), R$^1$=Benzyl, R$^2$=OCH$_3$, R$^3$=COOCH$_3$, a=double bond]

Following the procedure of Example 3, but using 2.80 g of 3-benzyl-1,7a-dihydro-9-methoxybenzofuro[3,2-e]isoquinolin-2,4-dione (from Example 8), there was obtained 3.23 g of a 13:1 mixture of two isomeric adducts as an oil. Crystallization of the crude oil from aceonitrile gave 1.66 g (48%) of the title compound as a single isomer. NMR spectrum (200 mHz in CDCl$_3$): δ1.2–1.85 (m, 1H), 1.9–2.1 (m, 1H), 3.0, 3.2 (ABq, J=18 Hz, 2H), 3.15 (m, 1H), 3.33 (s, 3H), 3.8 (s, 3H), 4.55 (d, J=3 Hz, 1H), 5.17 (s, 2H), 6.0 (d, J=7 Hz, 1H), 6.32 (s, 1H), 6.33 (d, J=2 Hz, 1H), 6.47 (t, J=7 Hz, 1H), 6.68 (d, J=9 Hz, 1H), 7.3–7.4 (m, 3H) and 7.5–7.7 (m, 2H).

EXAMPLE 10

3-Benzyl-1,3,5,6,7,7a-hexahydro-9-methoxy-5-methoxycarbonyl-4a,7-ethanobenzofuro[3,2-e]isoquinoline-2,4-dione [(XIII), R$^2$=Benzyl, $^3$R=OCH$_3$, R=COOCH$_3$, a=single bond]

Following the procedure of Example 4, but using 4.21 g of 3-benzyl-1,3,5,6,7,7a-hexahydro-9-methoxy-5-methoxycarbonyl-4a,7-ethenobenzofuro[3,2-e]isoquinolin-2,4-dione (from Example 9) and 2.0 g of 10% palladium on charcoal as starting materials, there was obtained 4.22 g (99%) of the title compound. NMR spectrum (200 mHz in CDCl$_3$): δ1.0–2.5 (m, 6H), 3.0 (m, 1H), 3.06 (d, J=3 Hz, 2H), 3.37 (s, 3H), 3.83 (s, 3H), 4.48 (d, J=2 Hz, 1H), 5.07 (s, 2H), 6.03 (d, J=6.7 Hz, 1H), 6.55 (t, J=6.7 Hz, 1H), 6.75 (d, J=6.7 Hz, 1H), 7.3–7.6 (m, 5H). IR spectrum: 1740 cm$^{-1}$, 1728 cm$^{-1}$, 1675 cm$^{-1}$, among others.

EXAMPLE 11

3-Benzyl-5-hydroxymethyl-1,2,3,4,5,6,7,7a-octahydro9-methoxy-4a,7-ethenobenzofuro[3,2-e]-isoquinoline [(II), R$^1$=Benzyl, R$^2$=OCH$_3$, R$^3$=CH$_2$OH, a=double bond]

Following the procedure of Example 5, but using 11.48 g of 3-benzyl-1,3,5,6,7,7a-hexahydro-9-methoxy-5-methoxycarbonyl-4a,7-ethenobenzofuro[3,2-e]isoquinolin-2,4-dione (from Example 9), there was obtained 7.62 g (76%) of the crude title compound. NMR spectrum (200 mHz in CDCl$_3$): δ0.7–4.0 (m, 18H), 4.4 (d, J=0.5 Hz, 1H), 5.55 (d, J=7 Hz, 1H), 6.18 (t, J=6 Hz, 1H), 6.65–6.75 (m, 2H), 7.1 (m, 1H) and 7.2–7.5 (m, 5H).

EXAMPLE 12

3-Benzyl-5-hydroxymethyl-1,2,3,4,5,6,7,7a-octahydro-9-methoxy-4a,7-ethanobenzofuro[3,2-e]-isoquinoline [(II), R$^1$=Benzyl, R$^2$=OCH$_3$, R$^3$=CH$_2$OH, a=single bond]

Following the procedure of Example 5 but using 7.3 g of 3-benzyl-1,3,5,6,7,7a-hexahydro-9-methoxy-5-methoxycarbonyl-4a,7-ethanobenzofuro[3,2-e]isoquinoline-2,4-dione (from Example 10), there was obtained 5.27 g (82%) of the crude title compound as an oil. NMR spectrum (200 mHz in CDCl$_3$): δ0.9–3.0 (m, 14H), 3.25 (d, J=10 Hz, 1H), 3.45 (d/d, J=8/2 Hz, 1H), 3.7–3.95 (m, 3H), 3.85 (s, 3H), 4.43 (s, 1H), 6.78 (d, J=2 Hz, 1H), 4.8 (s, 1H), 7.1–7.2 (m, 1H), 7.2–7.4 (m, 5H). IR spectrum (neat): 3600–3200 cm$^{-1}$ among others.

EXAMPLE 13

3-Cyclopropylmethyl-1,3,5,6,7,7a-hexahydro-9-methoxy-5-formyl-4a,7-ethenobenzofuro-[3,2-e]isoquinoline-2,4-dione [(XII), R$^1$=Cyclopropylmethyl, R$^2$=OCH$_3$, R$^3$=CHO, a=double bond]

A mixture of 0.10 g of the product of Example 2, 0.01 g of phenothiazine, and 1 ml of acrolein contained in an evacuated, sealed Carius tube was heated to 85°–87° for 16 hours. Removal of excess acrolein gave 0.22 g of crude product, the NMR spectrum of which showed the complete absence of starting material, and the presence of mostly a single isomer of the desired adduct. The product was isolated by chromatography on silica (elution with 2:1 hexane/ethyl acetate) to give the title compound. NMR spectrum (360 mHz in CDCl$_3$): δ0.4–0.6 (m, 4H), 1.3 (m, 1H), 1.8 (d/d/d, J=14.0/9.0/1.5 Hz, 1H), 2.1 (d/t, J=14/4 Hz, 1H), 2.9 (d/t, J=9.0/2.5 Hz, 1H), 3.0 (d, J=18 Hz, 1H), 3.3 (d, J=18 Hz, 1H), 3.4 (m, 1H), 3.8 (s, 3H), 3.85 (d/d, J=13/7 Hz, 1H), 3.95 (d/d, J=13/7 Hz, 1H), 4.6 (d, J=3.5 Hz), 6.3 (d/d, J=8/6 Hz, 1H), 6.4 (d, J=8 Hz, 1H), 6.6 (d/d, J=7/2 Hz, 1H), 6.7–6.8 (m, 2H), and 9.4 (d, J=2 Hz, 1H). Mass spectrum: m/z calcd. for C$_{23}$H$_{23}$NO$_5$, 393.1576; found, 393.1576.

EXAMPLE 14

3-Cyclopropylmethyl-1,3,5,6,7,7a-hexahydro-9-methoxy-5-formyl-4a,7-ethanobenzofuro-[3,2-e]isoquinoline-2,4-dione [(XIII), R$^1$=Cyclopropylmethyl, R$^2$=OCH$_3$, R$^3$=CHO, a=single bond]

Following the procedure of Example 4, but using 0.275 g of 3-cyclopropylmethyl-1,3,5,6,7,7a-hexahydro-9-methoxy-5-formyl-4a,7-ethenobenzofuro[3,2-e]isoquinolin-2,4-dione (from Example 13), there was obtained 0.26 g (94%) of a crude mixture of the title compound and the corresponding 5-hydroxymethyl ompound. The aldehyde had the following NMR Spectrum (200 mHz in CDCl$_3$): δ0.3–4.0 (m, 20H), 4.5 (s, 1H), 6.6–6.9 (m, 3H) and 9.68 (s, 1H); and IR spectrum: 1730 cm$^{-1}$, 1675 cm$^{-1}$, among others.

EXAMPLE 15

3-Cyclopropylmethyl-5-hydroxymethyl-9-methoxy-1,2,3,4,5,6,7,7a-octahydro-4a,7-ethanobenzofuro[3,2-e]isoquinoline [(II), R$^1$=Cyclopropylmethyl, R$^2$=OCH$_3$, R$^3$=CH$_2$OH, a=single bond]

A solution of 0.26 g of the product mixture from Example 14 in tetrahydrofuran was reduced with lithium aluminum hydride as described in Example 5 to give 0.17 g (70%) of oil, the NMR spectrum of which showed the major product to be identical with the title compound (U.S. Pat. No. 4,477,456, product of Example 5).

EXAMPLE 16

N-(n-Propyl)-N-(2-pyrone-6-carbonyl)-7-methoxy-3-benzofuranacetamide [(IX), R$^1$=n-Propyl, R$^2$=OCH$_3$]

Part A

Following the procedure of Example 1 Part B, but using 1.19 g of 7-methoxy-3-benzofuranacetic acid and 0.53 g of n-propylamide in place of cyclopropylmethylamine, and heating to 48° for 19 hours, there was obtained 1.07 g (96%) of N-(n-propyl)-7-methoxy-3-benzofuranacetamide as a solid. NMR spectrum (200 mHz in CDCl$_3$): δ0.8 (t, J=7 Hz, 3H), 1.4 (m, 2H), 3.15 (q, J=6 Hz, 2H), 3.63 (s, 2H), 4.0 (s, 3H), 5.5–5.7 (broad s, 1H), 6.85 (d/d, J=7.0/0.5 Hz, 1H) 7.1–7.3 (m, 2H) and 7.61 (s, 1H).

Part B

Following the procedure of Example 1 Part C, but using 1.24 g of N-n-propyl-7-methoxy-3-benzofuranacetamide, there was obtained 1.86 g (100%) of N-(n-propyl)-N-(2-pyrone-6-carbonyl)-7-methoxy-3-benzofuranacetamide. NMR spectrum (200 mHz in CDCl$_3$): δ0.95 (t, J=7 Hz, 3H), 1.6–1.9 (m, 2H), 3.72 (t, J=7 Hz, 2H), 4.00 (s, 3H), 4.02 (s, 2H), 6.45 (d, J=8 Hz, 1H), 6.75 (d/d, J=7.0/0.5 Hz, 1H), 6.83 (d/d, J=7.0/0.5 Hz, 1H), 7.1–7.3 (m, 2H), 7.4 (d/d, J=8.0/6.5 Hz, 1H) and 7.7 (s, 1H).

EXAMPLE 17

3-(n-Propyl)-1,7a-dihydro-9-methoxybenzofuro[3,2-e]isoquinoline-2,4-dione [(X), R$^1$=n-Propyl, R$^2$OCH$_3$]

Following the procedure of Example 2, but using 0.80 g of N-(n-propyl)-N-(2-pyrone-6-carbonyl)-7-methoxy-3-benzofuranacetamide (from Example 16), there was obtained 0.58 g (82%) of the title compound as an oil. NMR spectrum (200 mHz in CDCl$_3$): δ0.95 (t, J=7 Hz, 3H), 1.67 (m, 2H), 2.85, 2.95 (ABq, J=15 Hz, 2H), 3.9 (s, 3H), 3.8–4.0 (m, 2H), 5.5 (s, 1H), 6.0–6.3 (m, 2H), 6.45 (t, J=2.5 Hz, 1H), 6.79 (d, J=7 Hz, 2H) and 7.2 (d, J=7 Hz, 1H).

EXAMPLE 18

3-(n-Propyl)-1,3,5,6,7,7a-hexahydro-9-methoxy-5-methoxycarbonyl-4a,7-ethenobenzofuro[3,2-e]isoquinoline-2,4-dione [(XII), R$^1$=n-Propyl, R$^2$=OCH$_3$, R$^3$=COOCH$_3$, a=double bond]

Following the procedure of Example 3, but using 0.31 g of 3-(n-propyl)-1,7a-dihydro-9-methoxybenzofuro[3,2-e]isoquinoline-2,4-dione (from Example 17), there was obtained 0.31 g (79%) of the title compound as a mixture of two isomeric adducts. The NMR spectrum of the mixture showed the presence of mostly a single isomer of the desired adduct.

The major isomer had the following NMR spectrum (200 mHz in CDCl$_3$): δ1.0 (t, J=4 Hz, 3H), 1.6–1.9 (m, 3H), 2.0 (m, 1H), 2.95, 3.15 (ABq, J=18 Hz, 2H), 3.1 (m, 1H), 3.35 (m, 1H), 3.6 (s, 3H), 3.81 (s, 3H), 3.8–4.0 (m, 2H), 4.55 (d, J=1 Hz, 1H), 6.3–6.4 (m, 3H) and 6.65–6.75 (m, 2H).

EXAMPLE 19

3-Benzyl-1,3,5,6,7,7a-hexahydro-9-methoxy-benzofuro[3,2-e]isoquinoline-2,4-dione [(XI), R$^1$=benzyl, R$^2$=methoxy]

Following the procedure of Example 4 but using 0.05 g of the product of Example 8, there was obtained 0.03 g (60%) of the title compound. NMR spectrum (200 mHz in CDCl$_3$): δ1.3–2.4 (m, 6H), 2.75 (d, J=12 Hz, 1H), 2.75 (m, 1H), 3.05 (d, J=12 Hz, 1H), 3.85 (s, 3H), 4.55 (t, J=5 Hz, 1H), 4.93, 5.1 (ABq, J=11 Hz, 2H), 5.95 (d, J=7 Hz, 1H), 6.47 (t, J=7 Hz, 1H), 6.72 (d, J=7 Hz, 1H), 7.2–7.5 (m, 5H).

EXAMPLE 20

3-Benzyl-1,2,3,4,5,6,7,7a-octahydro-9-methoxy-benzofuro[3,2-e]isoquinoline [(I), R$^1$=benzyl, R$^2$=methoxy]

Following the procedure of Example 5 but using 0.03 g of the product prepared according to Example 19, there was obtained 0.05 g (180%) of crude oil, the NMR and IR spectrum of which were identical to those of the title compound prepared by the method of U.S. Pat. No. 4,243,668.

What is claimed is:

1. A compound having a formula selected from the group consisting of:

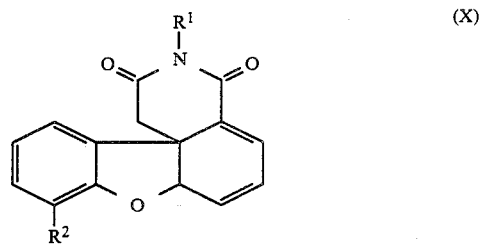

and

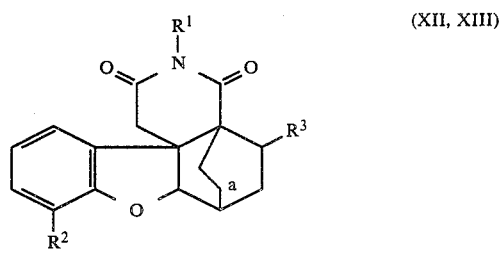

wherein
a is a single bond or double bond;
R$^1$ is C$_1$–C$_{10}$ alkyl, CH$_2$R$^6$, C$_2$H$_4$ (C$_6$H$_4$)R$^7$, or (CH$_2$)$_n$CN in which n=1–3;
R$^2$ is H, OH, or C$_1$–C$_2$ alkoxy;
R$^3$ is H, C$_1$–C$_8$ alkyl, or COR$^4$;
R$^4$ is H, C$_1$–C$_8$ alkoxy, or C$_1$–C$_8$ alkyl;
R$^6$ is CH=C(R$^8$)(R$^9$), C≡CH, C$_3$–C$_6$ cycloalkyl, phenyl, 2-thienyl, 2-furyl, 2-tetrahydrofuryl, methyl substituted 2-furyl, or methyl substituted 2-tetrahydrofuryl;
R$^7$ is H, C$_1$–C$_3$ alkyl, OCH$_3$, Cl, Br, or F; and
R$^8$ and R$^9$ are independently H, CH$_3$, or Cl.

2. The compound of claim 1 which is Formula (X) wherein
R$^1$ is C$_1$–C$_4$ alkyl, or CH$_2$R$^6$;
R$^2$ is H, OH, or C$_1$–C$_2$ alkoxy; and
R$^6$ is C$_3$–C$_6$ cycloalkyl, or phenyl.

3. The compound of claim 2 wherein R$^1$ is cyclopropylmethyl and R$^2$ is methoxy.

4. The compound of claim 2 wherein R$^1$ is n-propyl and R$^2$ is methoxy.

5. The compound of claim 2 wherein R$^1$ is benzyl and R$^2$ is methoxy.

6. The compound of claim 1 which is Formula (XII) wherein
a is a double bond;
R$^1$ is C$_1$–C$_4$ alkyl, or CH$_2$R$^6$;
R$^2$ is H, OH, or C$_1$–C$_2$ alkoxy;
R$^3$ is H, or COR$^4$;
R$^4$ is H, or C$_1$–C$_4$ alkoxy; and
R$^6$ is C$_3$–C$_6$ cycloalkyl, or phenyl.

7. The compound of claim 6 wherein
R$^1$ is cyclopropylmethyl,
R$^2$ is methoxy and
R$^3$ is methoxycarbonyl.

8. The compound of claim 6 wherein
R$^1$ is n-propyl,
R$^2$ is methoxy and $R^3$ is methoxycarbonyl.
9. The compound of claim 6 wherein
$R^1$ is benzyl;
$R^2$ is methoxy; and
$R^3$ methoxycarbonyl.
10. The compound of claim 1 which is Formula (XIII) wherein
a is a single bond;
$R^1$ is $C_1$–$C_4$ alkyl, or $CH_2R^6$;
$R^2$ is H, OH, or $C_1$–$C_2$ alkoxy;
$R^3$ is H, or $COR^4$;
$R^4$ is H, or $C_1$–$C_4$ alkoxy; and
$R^6$ is $C_3$–$C_6$ cycloalkyl, or phenyl.

11. The compound of claim 10 wherein
$R^1$ is cyclopropylmethyl;
$R^2$ is methoxy; and
$R^3$ is methoxycarbonyl.
12. The compound of claim 10 wherein
$R^1$ is n-propyl,
$R^2$ is methoxy and
$R^3$ is methoxycarbonyl.
13. The compound of claim 10 wherein
$R^1$ is benzyl,
$R^2$ is methoxy and
$R^3$ is methoxycarbonyl.

* * * * *